(12) United States Patent
Padeste et al.

(10) Patent No.: US 7,459,614 B2
(45) Date of Patent: Dec. 2, 2008

(54) METHOD FOR GENERATING AN ARTIFICIALLY PATTERNED SUBSTRATE FOR STIMULATING THE CRYSTALLATION OF A BIOMOLECULE THEREON AND METHOD FOR STIMULATING THE CRYSTALLIZATION OF BIOMOLECULES

(75) Inventors: Celestino Padeste, Baden (CH); Christian Kambach, Brugg (CH); Jens Grobrecht, Gebensdorf (CH); Harun Solak, Brugg (CH)

(73) Assignee: Paul Scherrer Institut, Villigen PSI (CH)

( * ) Notice: Subject to any disclaimer, the term of this patent is extended or adjusted under 35 U.S.C. 154(b) by 227 days.

(21) Appl. No.: 10/916,472

(22) Filed: Aug. 12, 2004

(65) Prior Publication Data

US 2007/0111256 A1  May 17, 2007

Related U.S. Application Data

(63) Continuation of application No. PCT/EP03/01221, filed on Feb. 7, 2003.

(30) Foreign Application Priority Data

Feb. 15, 2002  (EP)  .................. 02003534
May 14, 2002  (EP)  .................. 02010730

(51) Int. Cl.
  *C30B 7/00*   (2006.01)
  *C30B 19/00*  (2006.01)
  *G02B 27/00*  (2006.01)

(52) U.S. Cl. ............... 977/888; 117/58; 117/68; 359/577

(58) Field of Classification Search ............... None
See application file for complete search history.

(56) References Cited

U.S. PATENT DOCUMENTS 6,645,677 B1 * 11/2003 Sandstrom ............... 430/5
6,882,477 B1 *  4/2005 Schattenburg et al. ..... 359/577

FOREIGN PATENT DOCUMENTS

EP     0 997 780 A1     5/2000
WO   WO 01/92293 A2   12/2001
WO   WO 02/42731    *  5/2002

OTHER PUBLICATIONS

Chen et al., 50-nm x-ray lithography using synchrotron radiation, Journal of Vacuum Science technology B, vol. 12, Iss. 6, p. 3959-3964, 1994.*

Yang X M et al: "Guide self.-assembly of symmetric diblock copolymer films in chemically nanopatterned substrates"; Macromolecules, American Chemical Society Easton PA,US; Dec. 26, 2000; XP002223275; pp. 9575-9297; ISSN: 0024-9297.

* cited by examiner

*Primary Examiner*—John S. Brusca
*Assistant Examiner*—Karlheinz R Skowronek

(57) ABSTRACT

It is the aim of the invention to provide a technology for the stimulation of the crystallization of biomolecules contained in a liquid solution that leads to significant improvements in the reliability of crystal growth processes and shortens the time and the number of attempts to grow a certain biomolecule crystal, also under the condition that only very small amounts of the biomolecules are available.

28 Claims, 2 Drawing Sheets

METHOD FOR GENERATING AN ARTIFICIALLY PATTERNED SUBSTRATE FOR STIMULATING THE CRYSTALLATION OF A BIOMOLECULE THEREON AND METHOD FOR STIMULATING THE CRYSTALLIZATION OF BIOMOLECULES

CROSS REFERENCE TO RELATED APPLICATIONS

The present application is a continuation of international application PCT/EP03/01221, filed Feb. 07, 2003, which designated the United States and further claims priority to European patent applications 02003534.1 and 02010730.6, filed Feb. 15, 2002, and May 14, 2002, respectively. The aforementioned applications are herein incorporated by reference.

BACKGROUND OF THE INVENTION

The invention relates to a method for generating an artificially patterned substrate for stimulating the crystallation of a biomolecule. Further, the invention relates to a method for stimulating the crystallization of biomolecules from a liquid solution containing said biomolecules.

Generally, collecting information related to the structure of proteins and other biomolecules is becoming an important field of technology. With information on the three-dimensional structure of biomolecules, knowledge on many fundamental processes of life can be deepened and the working mechanisms of essential biological processes can be partially or fully elucidated. This knowledge may allow for the more efficient synthesis of bio-active compounds and the optimization of the development of pharmaceuticals.

For this reason, the determination of molecular structures of proteins is an immensely important task in biological research. The most common method so far for structure determination is X-ray diffraction, which requires proteins to be crystallized before they can be analysed. Protein crystals are often obtained only after lengthy and labour-intensive screening processes. A considerable number of proteins resist crystallization efforts or yield crystals of poor quality which are not suitable for structure determination. Current laboratory practices are largely based on empirical results rather than on a fundamental understanding of crystal nucleation and growth at a physical level.

In the under the Patent Cooperation Treaty (PCT) published international patent application WO 01/92293 A2 are methods for nano-crystallogenesis disclosed. The disclosure relates so far to methods for identifying crystallization conditions for biomolecules using e.g. a method and an apparatus for screening the phase behaviour in liquid gel or solid phase of such biomolecules, like proteins, peptides, other macromolecules or complexes thereof. This publication also discloses methods for the screening of crystallization conditions and for allowing crystals with higher quality to be grown. These results are achieved by establishing a method for identifying crystallization conditions for at least one biomolecule. This method subjects said biomolecule to a set of compositions in a sample volume of 1 to 100 nanoliters in order to induce or to allow each of said compositions to adopt at least one first condition possibly allowing said crystallization to occur and to detect whether crystallization has occurred or not. The screening disclosed in this publication is performed by differing the test conditions from each test volume to the next. An appropriate method for the preparation of a solid support medium containing wells with a volume of up to 100 nanoliter provides a layer of negative photoresist on a carrier body and applies a pattern to said photoresist. Afterwards UV-illumination is applied to the photoresist and then the non-illuminated parts of the photoresist are removed.

The main drawback of this disclosure is that the methods proposed do not give any contribution to a better fundamental understanding of the crystallization and growth of proteins and other macromolecules. These methods are based more or less on arbitrary screening approaches to explore the optimal condition for the crystallization of biomolecules. It has to be mentioned that this lack of awareness for the fundamentals of macromolecular crystallization is inherent to the current state of art in this field of research.

One of the most promising attempts in the last years has been published by X. M. Yang, R. D. Peters, P. F. Nealey, H. H. Solak, F. Cerrina, "Guided self assembly of Symmetric Diblock Copolymer films on chemically nanopatterned substrates, Macromolecules 33, p. 9575. This publication recently demonstrated the organization of macromolecules by chemical contrast of the surface of a substrate matching the natural periodicity of the molecular structures by guided self-assembly of block copolymers. Block copolymers naturally form periodic structures due to micro-phase forces. The resultant structures are not crystalline but they are both regular and periodic. In this study a Self Assembled Monolayer (SAM) coated Si wafer was subjected to X-ray interference lithography (XIL) to obtain a periodic surface structure with chemical contrast. The block copolymer was then deposited on this template surface and annealed to activate the micro-phase separation process. The block copolymers were observed to arrange their domains according to the artificial template structure which was designed to match the natural periodicity of the copolymer.

Unfortunately, this technology does not apply to the stimulation of the crystallization of biomolecules since the attraction of copolymer self assembly is induced by micro-phase forces and is supported by the fact that a sufficient amount of the material to be self assembled is available. Very often in the field of biomolecular research the determination of the conditions under which crystallogenesis of biomolecules is efficient suffers from another drawback, namely that the available amounts of the target biomolecules are severely limited. More often than not biomolecules are available only in minute quantities (micrograms or nanograms), generally obtained after long and tedious processes.

SUMMARY OF THE INVENTION

According to these main drawbacks in the current state of the art, it is the aim of the invention to provide a technology for the stimulation of the crystallization of biomolecules contained in a liquid solution that leads to significant improvements in the reliability of crystal growth processes and shortens the time and the number of attempts to grow crystals of a certain biomolecule, with particular emphasis on the case that only very small amounts of the biomolecule are available.

This task is solved according to the invention by a method for generating an artificially patterned substrate for stimulating the crystallation of a biomolecule, comprising:

a) treating a basic substrate for providing an artificially patterned substrate;
  i) generating said artificially patterned substrate by exposing X-ray-radiation to said basic substrate;
  ii) performing said exposing of the X-ray-radiation according to X-ray interference lithography technology;

With respect to a method for stimulating the crystallization of biomolecules from a liquid solution containing said biomolecules, this task is solved according to the invention by a method comprising:

a) treating a basic substrate for providing an artificially patterned substrate;
   i) generating said artificially patterned substrate by exposing X-ray-radiation to said basic substrate;
   ii) performing said exposing of the X-ray-radiation according to X-ray interference lithography technology;

b) bringing said artificially patterned substrate into contact with said solution for initiating the crystallization of said biomolecules on the pattern of the artificially patterned substrate.

These methods take advantage of the fact that the crystallization of the biomolecules can be induced by the interaction of the biomolecules with the surface of the artificially patterned substrate. This surface is so far characterized by the behaviour of the basic substrate under the illumination with X-rays carried out using X-ray lithography technology. This illumination will therefore depend on the material/chemical composition of the basic substrate and lead to a topographical and/or chemical contrast of this surface. While the artificially patterned surface is active in promoting crystal nucleation, crystal growth can be induced at solute concentrations where nucleation is expected not to occur spontaneously. For that reason, also for proteins where the nucleation proceeds too rapidly, artificial epitaxy can be used to achieve nucleation in a more controlled way under conditions where spontaneous nucleation does not occur such as lower supersaturation of the mother liquor.

To achieve excellent conditions for the stimulation of the crystallization the method might be adapted such that at least one lattice parameter of a crystal containing a number of said biomolecules is determined or already known, whereby the surface of the artificially patterned substrate is adjusted to this said at least one lattice parameter. This can be especially useful for production of protein crystals in a reproducible way for biotechnological or medical applications.

Excellent results are achieved when the dimension of the pattern matches at least approximately at least one lattice parameter of said crystal or when the dimension of the pattern is at least approximately an integer multiple of the at least one lattice parameter of said crystal or an integer part of at least one lattice parameter of said crystal. This measure allows the crystallization of the biomolecules on the regular and periodically patterned surface having mechanical and/or chemical contrast.

To provide a method that also allows determining the optimal structure of the artificially patterned substrate for a biomolecule whose lattice parameters are not or only roughly known, the method can be performed by generating a gradiential artificially patterned substrate having a gradient with respect to the periodicity of the pattern in at least one dimension of the surface of said gradiential artificially patterned substrate. This gradiential artificially patterned substrate allows to cover a certain range of lattice parameters. For instance, some rough idea about the range of the lattice parameter can be inferred from the size of the biomolecule and the gradient allows to design the surface to cover a certain range of periodicity around the expected or estimated period gained from the expected or estimated lattice parameters. The pattern derived thereof can be made to cover a certain period range with a certain frequency gradient so that locally the biomolecules are enabled to interact with a region of the surface having an approximately constant periodicity with a certain tolerance.

For this screening or determining process is might be most helpful, if the gradiential artificially patterned substrate has an average period and the periodicity has a variation in the range of 0.1 to 20% of the average period across the length and/or the width of the surface. For achieving surface areas with approximately constant periodicity and a sufficient number of periods it might be most appropriate if the periodicity varies in the range of 3 to 12%, preferably 5% or 10%, of the average period.

For example, when considering a variable period grating with an average period of 50 nm with 5% variation across the surface, i.e. covering a 1×1 mm² area, and under the assumption that the pattern period for succesful epitaxial nucleation has to be within an +/−0.1% interval around a certain period (e.g. 51 nm) then from calculation it can be derived that this requirement is satisfied within a 40 µm wide area encompassing approximately 800 periods of the grating. This can be deemed to be a large enough area for nucleation, given the observation that nuclei in protein crystal growth usually include several hundred molecules.

For this reason, the most suitable match of these requirements is obtained when the surface has an area in the range of 25 µm² to 25 mm². Typically, the area of the surface is in the range of 100 µm² to 10 mm², preferably approximately 1 mm². In accordance with the above, this area is large enough for the growth of the crystal to be expected in the region where the best match of the pattern with the natural crystalline form is obtained.

To describe this method in other words, the procedure is analoguous to search for the resonance response of an electrical or mechanical system by scanning the frequency of excitation and mesuring the response of the system. When the system is driven at the resonance frequency, then a large amplitude response is achieved. In the case of crystal growth the gradiential period structure will scan the "spatial frequency ranges" to find the resonance, i.e. the optimal match of the pattern with a natural crystal structure.

To generate a high capability of the artificially patterned substrate to structural analysis, for instance performed by X-ray diffraction means, the basic substrate is a transparent substrate, such as a standard glass cover slip. The glass material may additionally contribute to the success of this technology by its inert characteristics with respect to any chemical and/or catalytic impacts on the crystals to be nucleated and grown afterwards.

Nevertheless, one main advantage of this proposed technique is the flexibility of materials used as basic substrates for the subsequent patterning. This may lead to the conclusion that this technique is also very suitable in case of the basic substrate being of ceramic or metallic material, such as a thin layer of gold that allows to generate surfaces having solely or additionally a chemical contrast. For this reason, from various attempts it can turn out that the optimal growth conditions of the crystals are achieved with a surface having topographical contrast or having chemical contrast or having both topographical and chemical contrast.

Usually, the lattice parameters of proteins vary in the range of 5 to 100 nm. It is therefore adequate that the artificially generated pattern can be generated with a periodicity between 0.5 nm and 500 nm. A most appropriate periodicity is deemed to be achieved in the range of 1 to 100 nm. For periods larger than 30 to 40 nm it is easily possible to have a one-to-one match between the crystal and the surface pattern of the artificially patterned substrate. For smaller periods, for instance 10 nm, it is possible to match to an integer multiple of the biomolecule lattice parameter.

Additional advantageous variations of the inventions may be derived from the other dependent claims.

BRIEF DESCRIPTION OF THE SEVERAL VIEWS OF THE DRAWINGS

Examples of the invention are described with reference to the following drawing. Thereby, the drawing depicts.

DETAILED DESCRIPTION OF THE INVENTION

Figure 1:
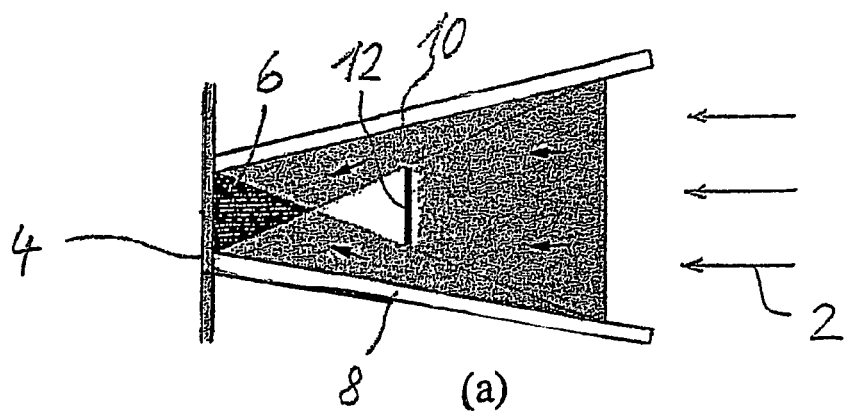
FIG. 1 a schematic view on three arrangements a) to c) of interference lithography with x-rays for generating an artificially patterned substrate.
Figure 1:
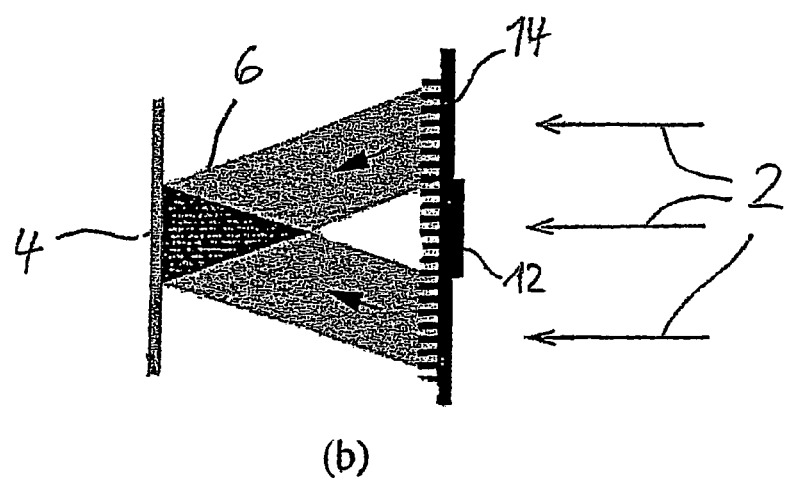
Figure 1:
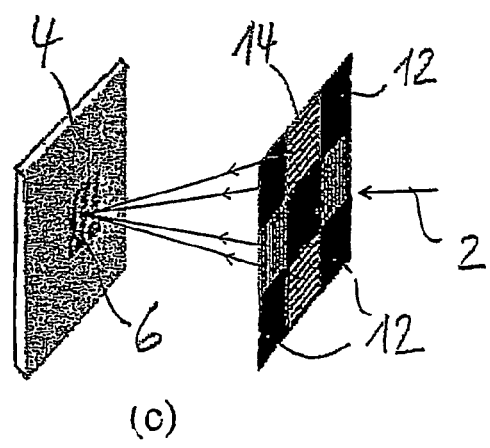

FIG. 1 shows schematically three different arrangements a) to c) of interference lithography technology with X-ray radiation 2 for generating an artifically patterned substrate 4 having a topographical patterned surface 6. In FIG. 1 a) an arrangement is shown having two grazing incidence mirrors 8, 10 which allow to a coherent X-ray beam to be deflected thereon and being by this deflection oriented towards the surface of a basic substrate having at the very beginning a more or less homogenous surface.

Due to the facts that the deflected beams are applied to the surface of the basic substrate under different angles the interference of these two beams is originated what leads to a grating pattern according to the interferencial behaviour of the two beams. After the illumination with this interferencial X-ray radiation the former homogeneous surface of the basic substrate became changed into the topographical patterned surface 6. The structure of the pattern, namely the periodicity of the pattern, depends thereby on the interferential pattern of the X-ray radiation, on the wave length of the X-ray radiation and on the angles with which the two beam are deflected by the mirrors 8, 10. To refrain the surface area illuminated with the interferential X-ray pattern from direct coherent X-ray illumination a direct beam stop element 12 is provided.

FIG. 1 b) depicts the second possible arrangement to generate the artifically patterned substrate 4 having a topographical surface 6. The grating pattern is hereby formed by two beams being diffracted by a linear grating 14. To generate the topographical surface 6 having a gradiental change of the periodicity in one dimension instead of a linear grating 14 a grating could be used that has a gradient in its structure, too. A topographical surface 16 having in one dimension a gradiential growth of the periodicity is shown in FIG. 2 a).

FIG. 1 c) last but not least shows a third possible arrangement for generating a two dimensional patterned topographical surface 6 on the then artificially patterned substrate 4. Four beams of the coherent X-ray radiation 2 are diffracted by linear gratings 14 and interfere afterwards when meeting under different angles and generate the interferential patterned topographical surface 6. Under the provision that the gratings 14 shows gradiential behaviour along the x- and y-axis a topographical surface 6 having a gradiential change of the periodicity in two dimensions as it is shown schematically in FIG. 2 b) can be obtained.

Figure 2:
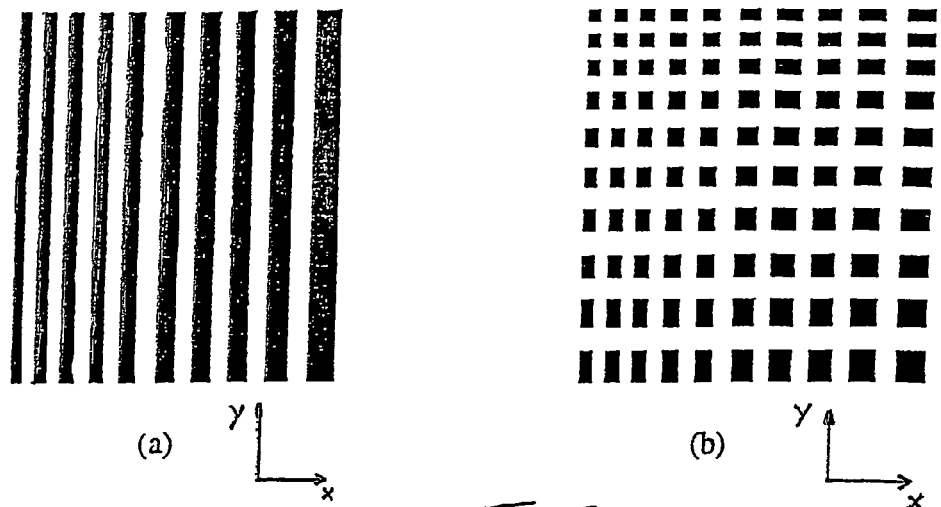
FIG. 2 a schematic partial view on two different artificially patterned substrates having a gradiental topographical surface.

The topographical surface according to FIG. 2 b) is best suitable for use in a process for screening or determining the optimal conditions for the stimulation of the crystallization of biomolecules on the topographical surface 6 since a more or less broad variation of the pattern allows the biomolecule to crystallize where the best match of its lattice parameters with the period of topographical surface 6 is provided.

On the other hand, in cases where lattice parameters and space group of a desired protein crystal are known a priori, the artificially patterned substrate 4 can be made with a pattern periodicity to match a certain crystal plane. Examples for this stimulation of the crystallization are schematically depicted in FIGS. 3 and 4.

Figure 3:
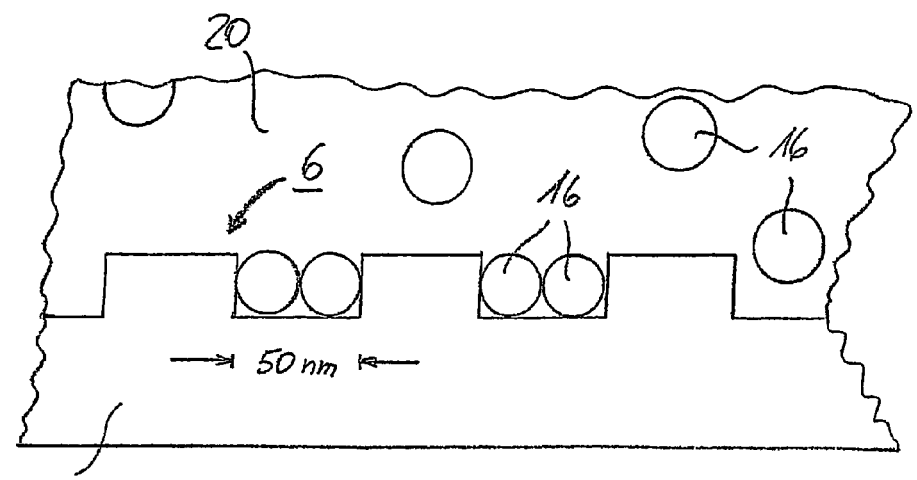
FIG. 3 a schematic partial view on a first artificially patterned substrate having a period of about 50 nm.

FIG. 3 thereby depicts a situation where the match of the period of the topographical surface 6 is an integer multiple, here four-fold, of the diameter of a mostly spherical protein molecule 16 which crystallizes in the wells of the topographical surface 6 having in this examples only a topographical contrast with respect to the periodicity of the wells. As far as the description of a surface having chemical contrast by means of a drawing is considered not to be possible in an appropriate manner only surfaces having topographical contrast are shown in the drawings. The situation shown in FIG. 3 should give a concept of initial crystal growth. After occupation of a certain number of adjacent wells, the next layers of crystallizing protein molecules 16 will connect the different nuclei stemming from the initial crystallization events and located in the different wells to form a crystal then spreading over a comparatively long range.

Figure 4:
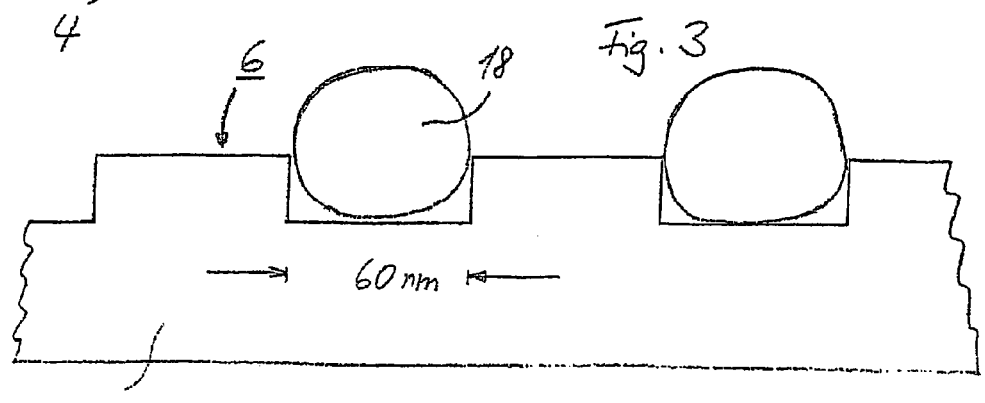
FIG. 4 a schematic partial view on a second artificially patterned substrate having a period of about 60 nm.

A corresponding situation is shown in FIG. 4, which illustrates a significant match of the dimensions of a second protein molecule 18 with the dimension of the artificially generated pattern of the substrate 4. In both cases according to the FIGS. 3 and 4 the period of the pattern lies in the middle of the usually existing range of biomolecule's lattice parameters.

Once the topographical patterned surfaces 6 are created and characterized they will be brought into contact with a solution 20 containing a certain concentration of the biomolecules 16 to be crystallized or containing an unknown composition of certain biomolecules. So they can be tested (initially) using standard protein or biomolecule growth configurations. If the patterned surfaces 6 are active in promoting crystal nucleation then the experiments can be conducted similar to micro-seeding ones.

The methods according to the invention allow the stimulation of the crystallization at solute concentration where nucleation usually can not be expected to occur spontaneously. This means that the amount of biomolecules 16, 18 for this experiment can be limited to very tiny amounts, e.g. an amount corresponding to the volume of a certain number of the wells (range of microliters and/or nanoliters). If the crystal nucleation is successful, e.g. whether the nucleation was truly epitaxial, could be varified by the orientational conformity between the topographical surface 6 and the crystal provided that the crystal does not detach from the topographical surface 6.

Finally, the methods according to the inventions envision the use of this technique in solving a number of nucleation related problems as mentioned in the very beginning of the description. In screening of growth conditions this technique leads to much quicker turnover times. For proteins where nucleation proceeds too rapidly due to the kinetical behaviour of the molecules and the therefrom derived danger of forming agglomerations in an amorphous form, artificial epitaxy can be used to achieve nucleation in a more controlled way under the conditions of an inclined supersaturation of the mother liquor. And in cases where the difficulties in the nucleation step causes restriction in the crystal growth altogether the technique induces nucleation and subsequent crystal growth of the desired crystall.

We claim:

1. A method for generating an artificially patterned substrate for stimulating crystallization of a biomolecule, comprising:
    treating a basic substrate for providing an artificially patterned substrate, wherein said basic substrate has a surface;
    arranging a grating at a predetermined distance to said surface and in a plane substantially parallel to said surface, the grating having a characteristic selected to generate a pattern of linear wells across said surface, wherein the pattern of linear wells has a gradient with respect to a pattern periodicity along a length and a width of said surface, and wherein the linear wells intersect;
    exposing the substrate through the grating to X-ray radiation to generate a gradiential artificially patterned substrate having said gradient; and
    performing said exposing according to X-ray interference lithography technology.

2. The method according to claim 1, wherein the pattern of the artificially patterned substrate is adapted to at least one lattice parameter of a crystal of said biomolecule by adjusting at least one of a wave length of the X-ray-radiation and interference conditions to a dimension of the pattern to be artificially generated.

3. The method according to claim 2, wherein the dimension of the pattern matches the at least one lattice parameter of said crystal.

4. The method according to claim 2, wherein the dimension of the pattern is at least one of an integer multiple of the at least one lattice parameter of said crystal and an integer part of the at least one lattice parameter of said crystal.

5. The method according to claim 1, wherein the gradiential artificially patterned substrate has an average period and the periodicity has a variation in the range of 0.1 to 20% of the average period.

6. The method according to claim 5, wherein the periodicity varies in the range of 3 to 12% of the average period.

7. The method according to claim 1, wherein the surface has an area in the range of 25 $\mu m^2$ to 25 $mm^2$.

8. The method according to claim 7, wherein the surface has an area in the range of 100 $\mu m^2$ to 10 $mm^2$.

9. The method according to claim 1, wherein the basic substrate is a transparent substrate.

10. The method according to claim 9, wherein the transparent substrate is a standard glass cover slip.

11. The method according to claim 1, wherein the basic substrate is one of a ceramic substrate and a metallic substrate.

12. The method according to claim 1, wherein the artificially generated pattern of the surface has a periodicity in the range of 0.5 mm to 500 nm.

13. The method according to claim 12, wherein the periodicity is in the range of 1 to 100 nm.

14. The method according to claim 1, wherein the biomolecules are proteins, peptides, macromolecules or complexes thereof.

15. A method for stimulating the crystallization of biomolecules from a liquid solution containing said biomolecules, comprising:
    providing a gradiential artificially patterned substrate having a pattern of liner wells extending across a surface of said substrate, wherein the pattern of linear wells has a gradient with respect to a pattern periodicity along a length and a width of said surface, and wherein the linear wells intersect; and
    bringing said gradiential artificially patterned substrate into contact with said liquid solution for initiating the crystallization of said biomolecules on the artificially patterned substrate.

16. The method according to claim 15, wherein the pattern of the artificially patterned substrate is adapted to at least one lattice parameter of a crystal containing a number of said biomolecules by adjusting at least one of a wave length of the X-ray-radiation and interference conditions to a dimension of the pattern to be artificially generated.

17. The method according to claim 16, the dimension of the pattern substantially matches the at least one lattice parameter of said crystal.

18. The method according to claim 16, wherein the dimension of the pattern is one of an integer multiple of the at least one lattice parameter of said crystal and an integer part of the at least one lattice parameter of said crystal.

19. The method according to claim 15, wherein the gradiential artificially patterned substrate has an average period and the periodicity has a variation in the range of 0.1 to 20% of the average period.

20. The method according to claim 19, wherein the periodicity varies in the range of 3 to 12% of the average period.

21. The method according to claim 20, wherein the surface has an area in the range of 25 $\mu m^2$ to 25 $mm^2$.

22. The method according to claim 21, wherein the surface has an area in the range of 100 $\mu m^2$ to 10 $mm^2$.

23. The method according to claim 22, wherein the basic substrate is a transparent substrate.

24. The method according to claim 23, wherein the transparent substrate is a standard glass cover slip.

25. The method according to claim 15, wherein the basic substrate is a ceramic substrate or a metallic substrate.

26. The method according to claim 15, wherein the artificially generated patterned substrate has a periodicity in the range of 0.5 nm to 500 nm.

27. The method according to claim 26, wherein the periodicity is in the range of 1 to 100 nm.

28. The method according to claim 15, wherein the biomolecules are proteins, peptides, macromolecules or complexes thereof.

* * * * *